(12) United States Patent
Chang

(10) Patent No.: US 11,701,093 B2
(45) Date of Patent: Jul. 18, 2023

(54) ULTRASOUND IMAGING DEVICE AND CLUTTER FILTERING METHOD USING SAME

(71) Applicant: ALPINION MEDICAL SYSTEMS CO., LTD., Hwaseong-si (KR)

(72) Inventor: Sun Yeob Chang, Seoul (KR)

(73) Assignee: ALPINION MEDICAL SYSTEMS CO., LTD., Hwaseong-si (KR)

( * ) Notice: Subject to any disclaimer, the term of this patent is extended or adjusted under 35 U.S.C. 154(b) by 689 days.

(21) Appl. No.: 16/646,252

(22) PCT Filed: Oct. 24, 2018

(86) PCT No.: PCT/KR2018/012597
§ 371 (c)(1),
(2) Date: Mar. 11, 2020

(87) PCT Pub. No.: WO2019/083263
PCT Pub. Date: May 2, 2019

(65) Prior Publication Data
US 2020/0275914 A1 Sep. 3, 2020

(30) Foreign Application Priority Data
Oct. 27, 2017 (KR) .......................... 10-2017-0140729

(51) Int. Cl.
*A61B 8/08* (2006.01)
*A61B 8/06* (2006.01)
(Continued)

(52) U.S. Cl.
CPC .............. *A61B 8/5269* (2013.01); *A61B 8/06* (2013.01); *A61B 8/488* (2013.01); *A61B 8/5223* (2013.01);
(Continued)

(58) Field of Classification Search
CPC ......... A61B 8/5269; A61B 8/06; A61B 8/488; A61B 8/5223; A61B 8/5276;
(Continued)

(56) References Cited

U.S. PATENT DOCUMENTS

| | | | | |
|---|---|---|---|---|
| 4,918,742 A | * | 4/1990 | Simonds | ................... G06T 5/20 382/304 |
| 7,729,747 B2 | * | 6/2010 | Stranc | ................ A61B 5/14551 600/475 |

(Continued)

FOREIGN PATENT DOCUMENTS

| | | |
|---|---|---|
| CN | 103473740 A | 12/2013 |
| CN | 104732493 A | 6/2015 |

(Continued)

OTHER PUBLICATIONS

Song, Pengfei, et al. "Ultrasound Small Vessel Imaging With Block-Wise Adaptive Local Clutter Filtering." *IEEE Transactions on Medical Imaging* vol. 36 Article 1 Jan. 2017 (3 pages in English).

(Continued)

*Primary Examiner* — Bo Joseph Peng
(74) *Attorney, Agent, or Firm* — NSIP Law

(57) ABSTRACT

An ultrasound imaging device and a clutter filtering method using the same are disclosed. The clutter filtering method using the ultrasound imaging device according to one embodiment includes obtaining ultrasound data from a field-of-view (FOV) of an object, generating decomposition data including common scale information by performing rank matrix decomposition once on all of the obtained ultrasound data, estimating local characteristic information by reflecting spatial information on each pixel to the common scale information, and extracting a blood flow signal by performing filtering on each pixel based on the estimated local characteristic information.

24 Claims, 10 Drawing Sheets

(51) Int. Cl.
  *G06T 5/00* (2006.01)
  *G06T 5/20* (2006.01)
  *G06T 7/00* (2017.01)
(52) U.S. Cl.
  CPC ............. *G06T 5/002* (2013.01); *G06T 5/20* (2013.01); *G06T 7/0012* (2013.01); *G06T 2207/10132* (2013.01); *G06T 2207/30104* (2013.01)
(58) Field of Classification Search
  CPC ......... A61B 8/5207; G06T 5/002; G06T 5/20; G06T 7/0012; G06T 2207/10132; G06T 2207/30104; G01S 7/52077; G01S 15/8981
  See application file for complete search history.

(56) References Cited

U.S. PATENT DOCUMENTS

| | | | |
|---|---|---|---|
| 8,684,934 B2 | 4/2014 | Kim | |
| 9,232,931 B2 | 1/2016 | Kim | |
| 2008/0181479 A1* | 7/2008 | Yang | A61B 8/08 600/443 |
| 2011/0118606 A1* | 5/2011 | Kim | G01S 15/8981 600/453 |
| 2011/0196222 A1* | 8/2011 | Behrend | A61B 5/0062 600/407 |
| 2011/0257545 A1* | 10/2011 | Suri | A61B 8/5223 600/508 |
| 2011/0275938 A1 | 11/2011 | Kim et al. | |
| 2012/0022372 A1* | 1/2012 | Kim | G01S 15/8981 600/437 |
| 2012/0075638 A1* | 3/2012 | Rollins | A61B 5/0066 356/479 |
| 2013/0094729 A1* | 4/2013 | Mauldin, Jr. | A61B 8/481 382/128 |
| 2014/0093150 A1* | 4/2014 | Zalev | A61B 5/7257 382/128 |
| 2014/0112544 A1* | 4/2014 | Yu | A61B 8/587 382/107 |
| 2014/0316274 A1 | 10/2014 | Koh et al. | |
| 2019/0053780 A1 | 2/2019 | Song et al. | |
| 2020/0178938 A1* | 6/2020 | Alizad | A61B 8/5246 |
| 2020/0275914 A1* | 9/2020 | Chang | A61B 8/5223 |

FOREIGN PATENT DOCUMENTS

| | | |
|---|---|---|
| JP | 2011-104354 A | 6/2011 |
| KR | 2000-0073096 A | 12/2000 |
| KR | 10-2011-0123596 A | 11/2011 |
| KR | 10-2012-0009928 A | 2/2012 |
| KR | 10-2014-0126227 A | 10/2014 |
| WO | WO 2017/146886 A1 | 8/2017 |

OTHER PUBLICATIONS

Notification of Grant dated Mar. 16, 2022 in counterpart Chinese Patent Application No. 201880062358.3 (4 pages in English, 4 pages in Mandarin).
Korean Notice of Allowance dated Mar. 8, 2018 in counterpart Korean Patent Application No. 10-2017-0140729 (2 pages in Korean).
International Search Report dated Jan. 22, 2019 in counterpart International Patent Application No. PCT/KR2018/012597 (2 pages in English and 2 page in Korean).

* cited by examiner

ULTRASOUND IMAGING DEVICE AND CLUTTER FILTERING METHOD USING SAME

CROSS REFERENCE TO RELATED APPLICATIONS

This application is a U.S. National Stage Application of International Application No. PCT/KR2018/012597, filed on Oct. 24, 2018, which claims the benefit under 35 USC 119(a) and 365(b) of Korean Patent Application No. 10-2017-0140729, filed on Oct. 27, 2017, in the Korean Intellectual Property Office, the entire disclosure of which is incorporated herein by reference for all purposes.

TECHNICAL FIELD

The present invention relates to a technique for imaging an ultrasound signal, and more particularly, to a clutter filtering technique necessary for imaging.

The present invention was supported by the National Research and Development Project having grant number: HI15C-1817-020015, department name: The Ministry of Health & Welfare, research management institution: Korea Health Industry Development Institute, research project name: Development of Medical Device Technology, research title: Development of Cardiovascular Imaging Device Incorporating Ultrasound Waves and Light Waves and Commercialization of Imaging System, contribution rate: 1/1, research supervising institution: Alpinion Medical System Co., Ltd., and research period: Sep. 1, 2018 to Jun. 30, 2019.

BACKGROUND ART

An ultrasound Doppler method that utilizes a commonly well-known Doppler effect is used to measure blood flow information. In order to measure the blood flow information, an ultrasound signal is transmitted to a human body, and when the transmitted signal is reflected back from blood, the reflected ultrasound signal is used. The reflected ultrasound signal includes a signal reflected from a tissue such as a blood vessel wall or the like in addition to a signal reflected from a red blood cell or the like in a blood vessel, thereby causing errors in calculating actual information on blood flow. A tissue signal or a noise signal reflected from a tissue, a muscle, or the like that is stationary or moves very slowly is defined as a clutter signal. A filter used to obtain a desired ultrasound Doppler signal from the reflected ultrasound signal, which is distorted, is referred to as a clutter filter. A filtering process using the clutter filter is referred to as clutter filtering. An ultrasound imaging device may separate a blood flow signal from an undesired clutter signal through the clutter filtering.

DISCLOSURE

Technical Problem

The present invention is directed to providing an ultrasound imaging device and a clutter filtering method using the same capable of achieving real-time imaging as well as filtering performance improvement by reducing the amount of computation used in a calculation.

Technical Solution

One aspect of the present invention provides a clutter filtering method using an ultrasound imaging device including obtaining ultrasound data from a field-of-view (FOV) of an object, generating decomposition data including common scale information by performing rank matrix decomposition once on all of the obtained ultrasound data, estimating local characteristic information by reflecting spatial information on each pixel to the common scale information, and extracting a blood flow signal by performing filtering on each pixel based on the estimated local characteristic information.

The rank matrix decomposition may be singular value decomposition (SVD), the SVD may be performed on an input data matrix of all of the ultrasound data to obtain decomposition data decomposed into scale information, spatial information, and time information, the scale information may be a singular value matrix composed of singular values representing scale values for each subspace, the spatial information may be a spatial vector matrix composed of spatial vectors corresponding to each of the singular values, and the time information may be a transposed matrix of a time vector matrix composed of time vectors corresponding to each of the singular values.

In the estimating of the local characteristic information, spatial vectors for each pixel constituting the spatial information may be combined with the common scale information to estimate the local characteristic information in which characteristics for each pixel are reflected.

The estimating of the local characteristic information may include generating a scale value curve by configuring scale values in the common scale information, and generating a local characteristic curve by transforming the generated scale value curve according to a spatial characteristic of each pixel.

The estimating of the local characteristic information may include performing filtering on the spatial vectors for each pixel constituting the spatial information in a spatial direction, and combining the filtered spatial vector for each pixel with the common scale information to generate local characteristic information of which the common scale information is transformed.

The estimating of the local characteristic information may further include adjusting a degree of combining between the spatial vector for each pixel and the scale information. The estimating of the local characteristic information may further include generating a characteristic curve by configuring characteristic values for each pixel, and converting the generated characteristic curve to have a log scale or a decibel scale. The estimating of the local characteristic information may further include at least one of performing a smoothing process on the generated characteristic curve using a smooth filter and performing a moving average process on the generated characteristic curve.

The extracting of the blood flow signal may include calculating cutoff threshold values that are different for each piece of the estimated local characteristic information and performing local adaptive filtering by reflecting each of the calculated cutoff threshold values to each pixel.

In the calculating of the cutoff threshold value, the cutoff threshold value may be calculated using a slope of each scale value order and an average slope in a section of a characteristic curve in each characteristic curve in which characteristics of each pixel are reflected.

In the calculating of the cutoff threshold value, for each characteristic curve, the average slope in the section of the characteristic curve may be subtracted from the slope in each scale value order, and the scale value order having a minimum value in the curve obtained by accumulating subtracted results may be determined as a low-order cutoff threshold value.

In the calculating of the cutoff threshold value, a characteristic curve of each pixel may be extended using characteristics of a scale value curve, and a low-order cutoff threshold value may be determined in the extended characteristic curve.

The extracting of the blood flow signal may further include evaluating the cutoff threshold values calculated for each pixel and adjusting the cutoff threshold values when the cutoff threshold values are not effective according to the evaluation result.

The evaluating of the cutoff threshold value may include obtaining a Doppler spectrum for time information generated through the rank matrix decomposition, comparing a frequency value of each time vector order of the obtained Doppler spectrum with a preset Doppler spectrum frequency value to set the time vector order whose frequency value is greater than the preset Doppler spectrum frequency value or the time vector order having a frequency value whose difference from the preset Doppler spectrum frequency value is less than a preset offset value as an effective value, and evaluating effectiveness of the cutoff threshold value according to whether the cutoff threshold value is greater or less than the effective value.

The evaluating of the cutoff threshold value may include obtaining a Doppler spectrum for time information generated through the rank matrix decomposition, comparing a frequency value of each time vector order of the obtained Doppler spectrum with a preset Doppler spectrum frequency value to set a section consisting of time vector orders whose frequency value is greater than the preset Doppler spectrum frequency value or the time vector order having a frequency value whose difference from the preset Doppler spectrum frequency value is less than a preset offset value as an effective range, and evaluating effectiveness of the cutoff threshold value according to whether the cutoff threshold value is included in the set effective range.

In the adjusting the cutoff threshold value, when the cutoff threshold value is not effective according to the evaluation result, the cutoff threshold value calculated using a scale value curve may be used as the cutoff threshold value of the corresponding pixel.

The performing of the local adaptive filtering may include generating a threshold value map composed of the calculated cutoff threshold values for each pixel and separating the blood flow signal from a clutter signal by performing filtering using the generated threshold value map. The performing of the local adaptive filtering may further include performing filtering on the generated cutoff map. In the separating of the blood flow signal, spatial vectors of a pixel having a cutoff threshold value less than a low-order cutoff threshold value or greater than a high-order cutoff threshold value for each pixel in the threshold value map may be masked to zero or the spatial vectors may be weighted by a predetermined value.

Another aspect of the present invention provides an ultrasound imaging device including a signal obtaining unit configured to transmit an ultrasound signal to an object and receive the ultrasound signal reflected from the object, and a processor configured to estimate local characteristic information by reflecting spatial information on each pixel to common scale information generated by performing rank matrix decomposition once on obtained ultrasound data and extract a blood flow signal by performing filtering on each pixel based on the estimated local characteristic information.

The processor may include a data decomposition unit configured to generate decomposition data including spatial information, time information, and common scale information by performing the rank matrix decomposition on all of the obtained ultrasound data, a data conversion unit configured to estimate the local characteristic information in which characteristics of each pixel are reflected by combining spatial vectors of the pixel constituting the spatial information with the common scale information, a cutoff calculation unit configured to calculate cutoff threshold values that are different for each piece of the estimated local characteristic information, and a filtering unit configured to perform local adaptive filtering by reflecting each of the calculated cutoff threshold values to each pixel.

The data conversion unit may include a combining unit configured to combine a spatial vector for each pixel constituting the spatial information with the common scale information to generate the local characteristic information of which the common scale information is transformed, and a combining adjusting unit configured to adjust a degree of combining the spatial vector for each pixel and the scale information for combining.

The cutoff calculation unit may calculate the cutoff threshold values using a slope of each scale value order and an average slope in a section of a characteristic curve in each characteristic curve in which characteristics of each pixel are reflected.

The filtering unit may generate a threshold value map composed of the calculated cutoff threshold values for each pixel and mask the spatial vectors of the pixel having a cutoff threshold value less than a low-order cutoff threshold value or greater than a high-order cutoff threshold value for each pixel in the threshold value map to zero or weight the spatial vectors with a predetermined value.

Advantageous Effects

A clutter filtering method using an ultrasound imaging device according to one embodiment can simultaneously achieve real-time imaging and filtering performance improvement by reducing the amount of computation used in a calculation. For example, a global singular value decomposition (SVD) method, in which rank matrix decomposition is performed once on all of the ultrasound data, and a local adaptive clutter filtering method are used together. Accordingly, it is possible to take advantage of both reduction of the amount of computation when using the global SVD method and filtering performance improvement when using the local adaptive clutter filtering.

Since SVD is performed only once for all of the data, computational load can be greatly reduced, thereby enabling real-time imaging. Furthermore, local characteristic information is estimated by reflecting spatial information on each pixel to a common singular value generated through SVD so that filtering can be performed pixel by pixel. That is, new characteristic values are generated by reflecting pixel-specific characteristics to the common singular value to transform the common singular value so that the local adaptive clutter filtering can be performed pixel by pixel.

MODES OF THE INVENTION

Figure 1:
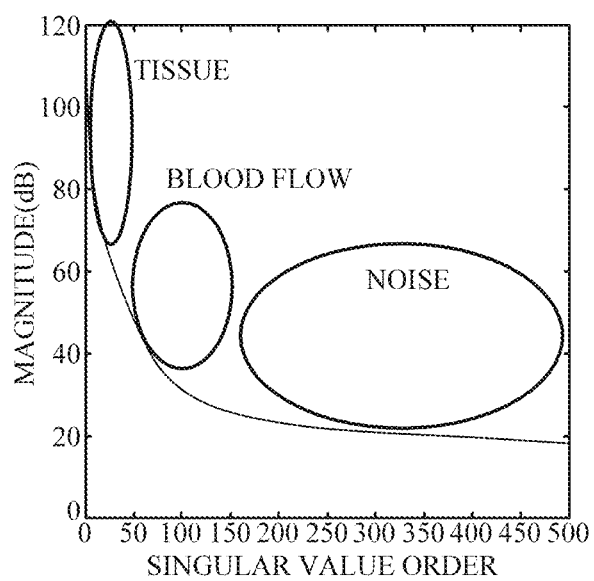
FIG. 1 is a graph illustrating a singular value curve obtained from ultrasound data for describing the concept of clutter filtering according to one embodiment of the present invention.

The advantages and features of the present invention and the manner of achieving the advantages and features will become apparent with reference to embodiments described in detail below together with the accompanying drawings. However, the present invention may be implemented in many different forms and should not be construed as being limited to the embodiments set forth herein, and the embodiments are provided such that this disclosure will be thorough and complete and will fully convey the scope of the present invention to those skilled in the art, and the present invention is defined only by the scope of the appended claims. The same reference numerals refer to the same components throughout this disclosure.

In the following description of the embodiments of the present invention, if a detailed description of related known functions or configurations is determined to unnecessarily obscure the gist of the present invention, the detailed description thereof will be omitted herein. The terms described below are defined in consideration of the functions in the embodiments of the present invention, and these terms may be varied according to the intent or custom of a user or an operator. Therefore, the definitions of the terms used herein should follow contexts disclosed herein.

Combinations of each block of the accompanying block diagrams and each step of the accompanying flowcharts may be performed by computer program instructions (an execution engine), and these computer program instructions may be embedded in a processor of a general-purpose computer, a special purpose computer, or other programmable data processing equipment. Thus, these computer program instructions, which are executed through a processor of a computer or other programmable data processing equipment, produce tools for performing a function described in each block of the block diagrams or in each step of the flowcharts.

These computer program instructions may also be stored in a computer usable or readable memory which can be oriented toward a computer or other programmable data processing equipment so as to implement the function in a particular manner. Therefore, the computer program instructions stored in the computer usable or readable memory may produce an article of manufacture containing an instruction tool for performing the function described in each block of the block diagrams or in each step of the flowcharts.

Further, the computer program instructions can also be mounted on a computer or other programmable data processing equipment. Therefore, the computer program instructions which serve to operate a computer or other programmable data processing equipment by performing a series of operation steps on the computer or the other programmable data processing equipment to produce a computer-implemented process may also provide steps for executing the functions described in each block of the block diagrams and in each step of the flowcharts.

Further, each block or each step may represent a module, a segment, or a part of a code, which includes one or more executable instructions for performing specified logical functions, and it should be noted that, in some alternative embodiments, the functions described in the blocks or steps may occur out of sequence. For example, two blocks or steps shown in succession may in fact be substantially executed at the same time, and the two blocks or steps may also be executed in the reverse order of the corresponding function as necessary.

Hereinafter, embodiments of the present invention will be described in detail with reference to the accompanying drawings. However, the present invention may be realized in various forms, and the scope of the present invention is not limited to such embodiments. The embodiments of the present invention are provided to aid those skilled in the art in the explanation and the understanding of the present invention.

FIG. 1 is a graph illustrating a singular value curve obtained from ultrasound data for describing the concept of clutter filtering according to one embodiment of the present invention.

The clutter filtering is essential in imaging an ultrasound signal for small vessels. A blood flow signal may be separated from an undesired clutter signal through the clutter filtering. In order to distinguish the blood flow signal that has been difficult to distinguish in a conventional color Doppler ultrasound imaging device configured to measure blood flow images using a Doppler effect, an ultrasound imaging device according to one embodiment performs rank matrix decomposition-based clutter filtering. When an obtained ultrasound input signal is converted into the form of an input data matrix and rank matrix decomposition is performed on the input data matrix, the input data matrix may be decomposed into three matrices. The rank matrix decomposition performs at least one of Karhunen-Loeve transform (hereinafter referred to as "KLT"), singular value decomposition (hereinafter referred to as "SVD"), eigenvalue decomposition (hereinafter referred to as "EVD"), principal component analysis (hereinafter referred to as "PCA"), and the like. Hereinafter, although a description will be given by focusing on the SVD, the rank matrix decomposition is not limited to the SVD and may be equally applied to the KLT, the EVD, the PCA, and the like.

A blood flow signal is separated from a tissue signal or a noise signal in an image, in which tissue and noise characteristics change spatially, through the rank matrix decomposition-based clutter filtering. For example, as illustrated in FIG. 1, a singular value curve is generated by sequentially sorting singular values, which are generated by performing the SVD on the input data matrix, in descending order with respect to the magnitude (dB) of a singular value order. In the generated singular value curve, the tissue signal is typically present in a high spectral component (i.e., a high singular value) due to high speckle intensity and time consistency thereof. The noise signal is found at a lower spectral component (i.e., a low singular value) due to relatively low speckle intensity and time consistency thereof. The tissue signal, the blood flow signal, and some noise signals may be easily separated from each other through the SVD and singular value thresholding (SVT). The SVT means performing filtering on the tissue signal by distinguishing the tissue signal from the blood signal using a low-order cutoff threshold value and performing filtering on the noise signal by distinguishing the noise signal from the blood signal using a high-order cutoff threshold value.

The SVD for the clutter filtering includes a global SVD method and a block-wise SVD method. In the global SVD method, the SVD is performed on a data set obtained from the entire field-of-view (FOV) to obtain one singular value curve. Filtering is performed by obtaining one low-order cutoff threshold value or one high-order cutoff threshold value from the entire FOV using the singular value curve. In the global SVD method, a slow blood flow signal is expressed by maintaining a signal slower than high pass filtering. The SVD is performed on the entire FOV of an image to generate a unique singular value for all pixels and to calculate a unique threshold value for all the pixels so that the same threshold value is used for all the pixels. Accordingly, in the global SVD method, since filtering is performed using one threshold value, the performance degradation of the clutter filter, for example, a tissue signal partially remaining at a specific pixel position or a blood signal being filtered, is caused.

On the contrary, in the block-wise SVD method, the FOV is divided into a plurality of sub blocks, the SVD is performed on each of the divided sub blocks, and local adaptive filtering is performed by calculating a threshold value for each of the sub blocks, thereby improving filtering performance. However, in the block-wise SVD method, the computational load is too high due to a very large number of instances of SVD processing as compared with the global SVD method, and thus real-time imaging is impossible. For example, thousands of SVD calculations are required.

The ultrasound imaging device according to one embodiment proposes a method of performing the rank matrix decomposition once on all of the ultrasound data for the real-time imaging That is, instead of dividing the ultrasound data into several blocks and performing the SVD for each block, the SVD is performed once for all of the ultrasound data. Accordingly, the singular value is not generated for each block by the SVD, rather, only one singular value that is common to all blocks is generated by the SVD. In the case of performing the SVD for each block, the SVD is performed on the basis of the number of blocks to generate singular values for each block, and thus the computational load is too high. However, when SVD is performed only once for all of the data, only one singular value is generated, and filtering is performed using one singular value so that the computational load is greatly reduced, thereby enabling real-time imaging.

The ultrasound imaging device according to one embodiment uses a local adaptive clutter filtering method to enhance the filtering performance in addition to achieving real-time imaging by reducing the computational load. In the case of the global SVD, since the SVD is performed once for the entire FOV of the image, only one singular value common to all pixels is generated. Accordingly, since only one threshold value is calculated from the singular value curve and filtering is performed using one threshold value, the performance degradation of the clutter filter, for example, the tissue signal partially remaining or the blood signal being excessively filtered, is caused. In the ultrasound imaging device according to one embodiment, local characteristic information is estimated by reflecting the spatial information of each pixel to the common singular value generated through the SVD so that filtering may be performed pixel by pixel. That is, new characteristic values are generated by reflecting pixel-specific characteristics to the common singular value to transform the common singular value so that the local adaptive clutter filtering may be performed pixel by pixel.

As described above, the ultrasound imaging device according to one embodiment performs the global SVD on all of the image data and also uses the local adaptive filtering method. Such a method is referred to as a global SVD-based local adaptive filtering method.

Figure 2:
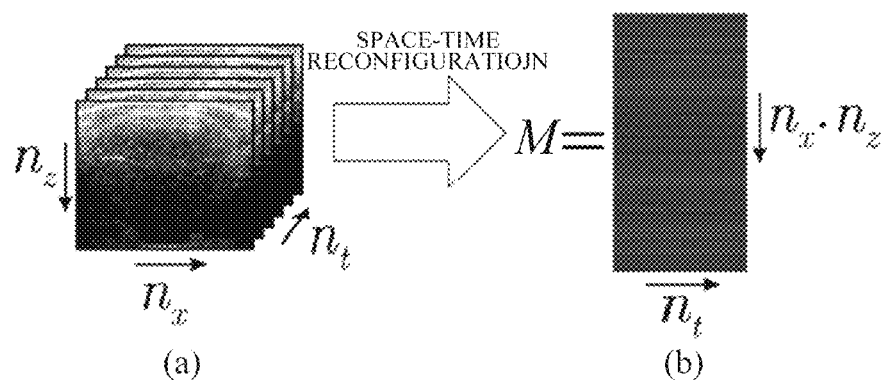
FIG. 2 is a reference diagram illustrating an input data set that is a target of rank matrix decomposition according to one embodiment of the present invention.

FIG. 2 is a reference diagram illustrating an input data set that is a target of the rank matrix decomposition according to one embodiment of the present invention.

Referring to FIG. 2, the input data set for the rank matrix decomposition is reconfigured from a three-dimensional form to a two-dimensional form. The ultrasound imaging device generates an image showing blood flow in a small blood vessel in an object based on ultrasound data. The obtained ultrasound data may be expressed as an input data matrix M having a rank K. The input data matrix M is a three-dimensional matrix ($N_x$, $N_z$, and $N_t$) having two dimensions ($N_x$ and $N_z$) associated with spatial direction and one dimension ($N_t$) associated with time direction and is the same as shown in FIG. 2A. $N_x$ is a scanline, $N_z$ is a sample, and $N_t$ is a slow-time. The three-dimensional input data matrix M may be reconfigured as a two-dimensional data set matrix ($N_x \times N_z$ and $N_t$) having one dimension ($N_x \cdot N_z$) in space and one dimension ($N_t$) in time and is the same as that shown in FIG. 2B. The two-dimensional matrix M having the rank K may be decomposed into three matrices, which are U, $\Sigma$, and $V^T$, through the rank matrix decomposition. Generally, such a process generates decomposition values based on the input data matrix M. For example, when the EVD is performed, the decomposition values are eigenvalues. As another example, when the SVD is performed, the decomposition values are singular values.

U of $U \cdot \Sigma \cdot V^T$ that are generated by decomposing the input data matrix M is spatial information, $\Sigma$ thereof is scale information, and $V^T$ thereof is time information. In the case of the SVD, $\Sigma$ is a singular value matrix composed of singular values representing scale values for each subspace, U is a spatial vector matrix U composed of spatial vectors corresponding to each of the singular values, and $V^T$ is a transposed matrix of a time vector matrix V composed of time vectors corresponding to each of the singular values. U and V are each a singular vector corresponding to the singular value. The singular vector may be a unitary vector. U may be referred to as a left singular vector, and V may be referred to as a right singular vector. $\Sigma$ is a diagonal matrix.

U(i) and V(i) are i-th columns of the matrix M, and $\lambda_i$, which is a diagonal element of $\Sigma$, is an ordered singular value. The number of $\lambda_i$ other than 0 is exactly the rank of the matrix M. Each column of V(i) corresponds to a time signal having a length $n_t$, and each column of U(i) corresponds to a spatial signal having the length $n_r$.

Referring to the meaning of $M = U \cdot \Sigma \cdot V^T$, one input data matrix of M is decomposed into a matrix having three characteristics, and the three transformed characteristics are combined to be the input data matrix M. It can be seen that the input data matrix M was combined by U(rotation transformation)+$\Sigma$(scale transformation)+V(rotation transformation). For example, it can be seen that rotation occurs due to V, the length of an axis changes due to Σ, and the rotation occurs again due to U so that the final M is generated.

Figure 3:
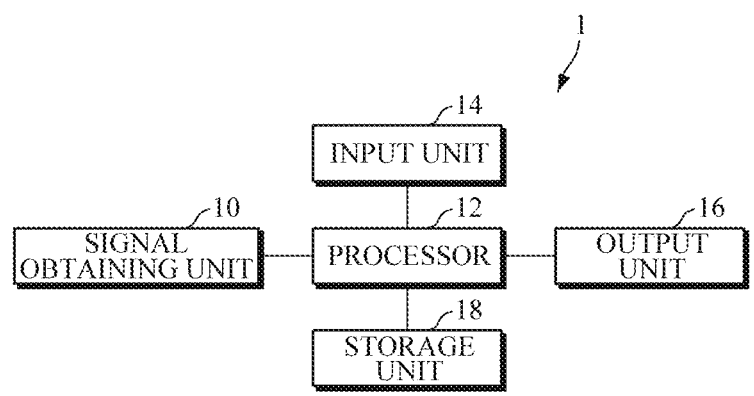
FIG. 3 is a block diagram of an ultrasound imaging device according to one embodiment of the present invention.

FIG. 3 is a block diagram of the ultrasound imaging device according to one embodiment of the present invention.

Referring to FIG. 3, an ultrasound imaging device 1 includes a signal obtaining unit 10, a processor 12, an input unit 14, an output unit 16, and a storage unit 18.

The signal obtaining unit 10 transmits an ultrasound signal to an object and receives the ultrasound signal (i.e., an ultrasound echo signal) reflected from the object. Data is obtained in a manner in which the ultrasound signal is repeatedly transmitted and received a predetermined number of times while fixing a scan line and repeatedly transmitted and received a predetermined number of times after moving to the next scan line. Assuming that there are N scan lines and M sample volumes and that the signal is transmitted L times for one scan line in order to obtain data for one scan line, each time the signal is transmitted, M sample volume data is obtained. Here, in each sample volume, the data obtained at the first transmission is referred to as ensemble 1 data, and the data obtained at the second transmission is referred to as ensemble 2 data. Here, the obtained data may be raw data, for example, in-phase/quadrature-phase (I/Q) data. The I/Q data includes a Doppler component as well as a clutter component.

The signal obtaining unit 10 sequentially and repeatedly performs a process of forming a transmission signal based on an ensemble number to generate a plurality of transmission signals. In addition, the signal obtaining unit 10 converts the generated transmission signal into an ultrasound signal and transmits the converted ultrasound signal to the object and then converts the ultrasound echo signal into a digital signal when the ultrasound echo signal reflected from the object is received. The converted ultrasound echo signal may be an I/Q signal.

The storage unit 18 stores operation processes of the ultrasound imaging device 1 according to one embodiment of the present invention, and the storage unit 18 may be implemented as at least one of a general hard disk, random access memory (RAM), and read-only memory (ROM).

The processor 12 generates an input data matrix M for the I/Q signal converted and output by the signal obtaining unit 10 and performs the SVD on M to generate $U \cdot \Sigma \cdot V^T$. The processor 12 forms a color flow image of an ultrasound image using $U \cdot \Sigma \cdot V^T$ and transmits the formed color flow image to the output unit 16.

The input unit 14 provides an interface for receiving a user's input information. In one embodiment, the interface enables a user to select information on the size and position of a FOV, that is, a color box, set on a brightness mode (B mode) image of an object. The input unit 14 may include a control panel, a mouse, a keyboard, and the like. The output unit 16 displays the color flow image formed by the processor 12 on a user's screen.

Figure 4:
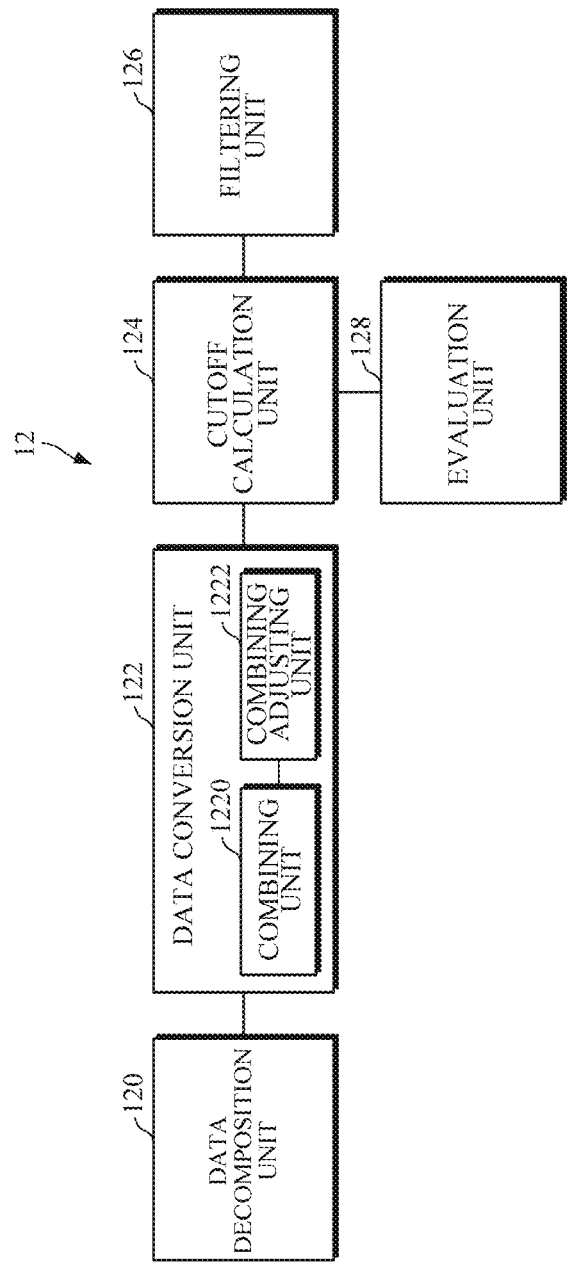
FIG. 4 is a detailed block diagram of a control unit in FIG. 3 according to one embodiment of the present invention.

FIG. 4 is a detailed block diagram of the control unit of FIG. 3 according to one embodiment of the present invention.

Referring to FIGS. 3 and 4, the processor 12 includes a data decomposition unit 120, a data conversion unit 122, a cutoff calculation unit 124, a filtering unit 126, and an evaluation unit 128.

The data decomposition unit 120 performs the rank matrix decomposition, for example, the SVD, on the input data matrix M representing all of the ultrasound data obtained through the signal obtaining unit 10 to generate decomposition data including spatial information U, time information $V^T$, and scale information Σ. The scale information Σ is a unique matrix value common to all pixels. That is, each pixel does not have different scale information Σ, but all pixels have one piece of scale information Σ that is commonly used. The pixel may be replaced with any area, and even in this case, the scale information Σ becomes a unique matrix value commonly used in all areas.

The data conversion unit 122 combines spatial vectors U(i) of the pixels constituting the spatial information with the common scale information Σ to estimate the local characteristic information Σ'(i) in which the characteristics for each pixel are reflected. The local characteristic information Σ'(i) is information obtained by transforming the scale information Σ according to the characteristics for each pixel. When the process of generating the local characteristic information Σ'(i) by transforming the scale information Σ is expressed differently, a scale value curve (a singular value curve in the SVD) is generated by configuring scale values (singular values in the SVD) in the scale information, and a local characteristic curve is generated by transforming the scale value curve according to the spatial characteristics for each pixel. A cutoff threshold value is calculated for each generated local characteristic curve to perform local adaptive filtering.

The data conversion unit 122 according to one embodiment includes a combining unit 1220 and a combining adjusting unit 1222. The combining unit 1220 combines an absolute value abs(U(i)) of the spatial vector U(i) for each pixel constituting the spatial information U and the scale information Σ to generate the local characteristic information Σ'(i). The combining adjusting unit 1222 adjusts the degree of combining the spatial vector U(i) for each pixel and the scale information Σ. For example, the combining adjusting unit 1222 adjusts the multiplier of the absolute value abs(U(i)) of the spatial vector for each pixel to adjust the degree of combining.

The cutoff calculation unit 124 calculates cutoff threshold values which are different from each other for the characteristic value of each pixel estimated by the data conversion unit 122. The cutoff threshold values for each pixel include at least one of a low-order cutoff threshold value and a high-order cutoff threshold value. The low-order cutoff threshold value is a threshold value for distinguishing the blood flow signal from the tissue signal, and the high-order cutoff threshold value is a threshold value for distinguishing the blood flow signal from the noise signal.

The cutoff calculation unit 124 according to one embodiment generates a characteristic curve by configuring characteristic values for each pixel and calculates a cutoff threshold value by using a slope of each scale value order in the characteristic curve and an average slope in a section of the characteristic curve. For example, in a predetermined characteristic curve, the average slope in the section of the characteristic curve is subtracted from the slope in each scale value order, and the scale value order having a minimum value in the curve obtained by accumulating subtracted results is determined as the low-order cutoff threshold value. As another example, when it is necessary to estimate the low-order cutoff threshold value by calculating only a partial section in the characteristic curve, the characteristic curve of each pixel may be extended using the characteristics of the scale value curve, and the low-order cutoff threshold value may be determined in the extended characteristic curve.

The evaluation unit 128 evaluates the cutoff threshold value calculated for each pixel by the cutoff calculation unit 124. When the cutoff threshold value is not effective according to the evaluation result, the cutoff calculation unit 124 may adjust the cutoff threshold value.

The evaluation unit 128 according to one embodiment obtains a Doppler spectrum for the time information V generated through the rank matrix decomposition. In addition, a frequency value of each time vector order of the obtained Doppler spectrum is compared with a preset Doppler spectrum frequency value, and the time vector order whose frequency value is greater than the preset Doppler spectrum frequency value or the time vector order having a frequency value whose difference from the preset Doppler spectrum frequency value is less than a preset offset value is set as an effective value. Next, the effectiveness of the cutoff threshold value is evaluated according to whether the cutoff threshold value is greater or less than the effective value.

As another example, the evaluation unit 128 obtains a Doppler spectrum for the time information generated through the rank matrix decomposition. In addition, a frequency value of each time vector order of the obtained Doppler spectrum is compared with a preset Doppler spectrum frequency value, and a section consisting of time vector orders whose frequency value is greater than the preset Doppler spectrum frequency value or the time vector order having a frequency value whose difference from the preset Doppler spectrum frequency value is less than a preset offset value is set as an effective range. Subsequently, the effectiveness of the cutoff threshold value is evaluated according to whether the cutoff threshold value is included in the set effective range.

When the cutoff threshold value is not effective according to the evaluation result of the evaluation unit 128, the cutoff calculation unit 124 may adjust the cutoff threshold value. For example, when the cutoff threshold value is not effective according to the evaluation result, the cutoff threshold value calculated using the scale value curve is used as a cutoff threshold value of the corresponding pixel.

The filtering unit 126 performs the local adaptive filtering by reflecting each cutoff threshold value calculated by the cutoff calculation unit 124 to each pixel. The filtering unit 126 according to one embodiment generates a threshold value map composed of the cutoff threshold values for each pixel. In addition, the blood flow signal is separated from the clutter signal by performing filtering using the generated threshold value map. Here, the filtering may be performed on the generated cutoff map. The filtering may include smoothing, median, weighting, and the like.

The filtering unit 126 according to one embodiment masks the spatial vectors for each pixel having a cutoff threshold value less than the low-order cutoff threshold value or greater than the high-order cutoff threshold value for each pixel in the threshold value map to zero or weights the spatial vectors to have a smaller value.

Figure 5:
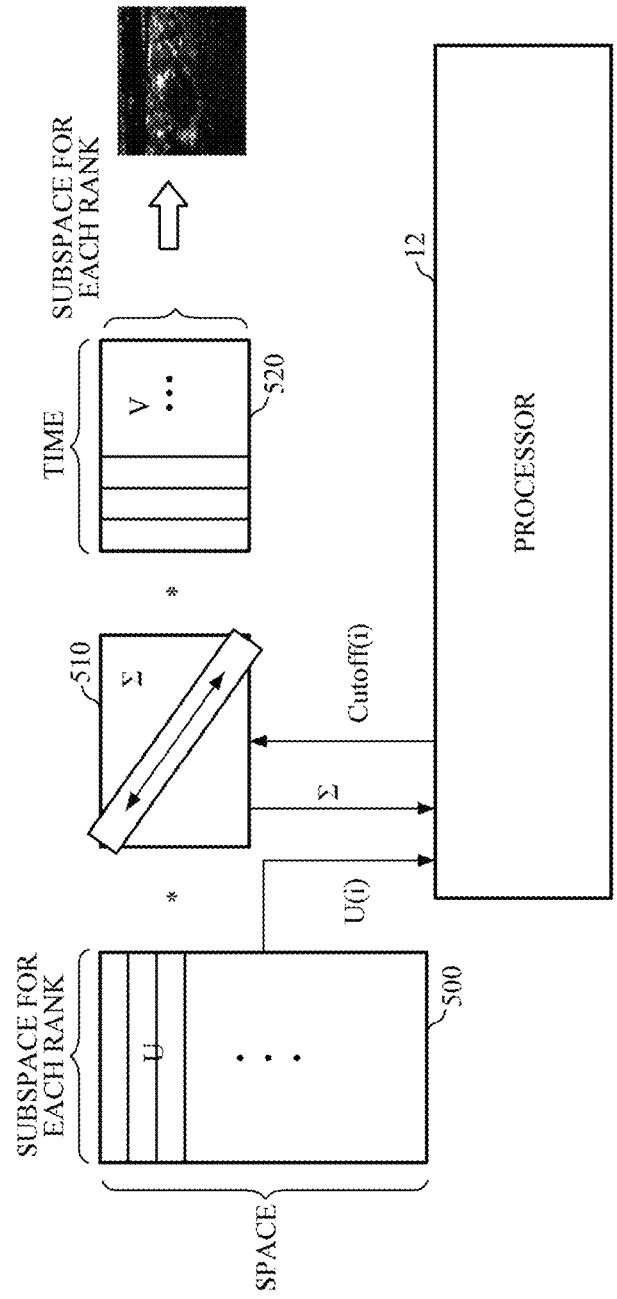
FIG. 5 is a reference diagram for describing a process of generating characteristic information according to one embodiment of the present invention.

FIG. 5 is a reference diagram for describing a process of generating characteristic information according to one embodiment of the present invention.

Referring to FIGS. 3 and 5, the processor 12 transforms the common scale information Σ to generate new local characteristic information Σ'(i). When a description is given using the SVD as an example, the new local characteristic information Σ'(i) is obtained by combining a singular value matrix 510 (Σ), which is obtained by performing the SVD on the input data matrix M, and a singular vector U(i) for each pixel. For example, each part of U, that is, U(1), U(2), U(3), . . . , is multiplied by a common Σ in sequence. When the SVD is performed, the common singular value matrix 510 (Σ), a spatial singular vector matrix 500 (U), and a time singular vector matrix 520 ($V^T$) are generated, and the common singular value 510 (Σ) may be expressed by a singular value curve composed of singular values. The local characteristic information Σ'(i) generated by combining the singular vector 500 (U(i)) for each pixel with the common singular value matrix 510 (Σ) may be expressed by a characteristic curve having a feature point for each pixel.

The processor 12 according to one embodiment combines an absolute value abs(U(i)) of the singular vector U(i) for each pixel and the singular value matrix Σ. The singular vector U(i) for each pixel, which is to be multiplied by the singular value matrix Σ, may be filtered in the spatial direction. Here, the filtering may include smoothing, averaging, median, and the like. The obtained characteristic curve may have a scale converted to a log scale or a decibel scale. The above-described process is expressed by an equation below, Σ'(i)=dB(Smooth(abs(U(i))*diag(Σ)). The obtained characteristic curve may be subjected to an averaging process, for example, a moving average process. As another example, the obtained characteristic curve may be subjected to a smoothing process using a smooth filter. The smooth filter may be an S-Golay filter. Depending on the smoothing method, the smoothing process may be performed before being converted to the log scale or the decibel scale.

In the characteristic curve, the portion enhanced due to the blood flow signal may be a feature point for the low-order cutoff threshold value. Once each local characteristic curve Σ'(i) is generated, the processor 12 estimates a cutoff threshold Cutoff(i) for each local characteristic curve.

Figure 6:
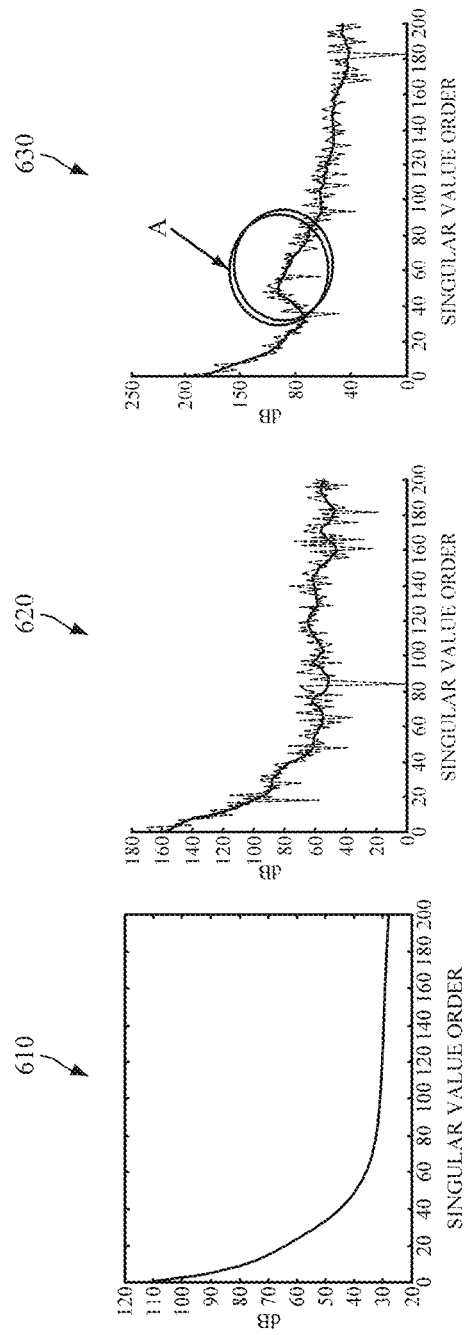
FIG. 6 is a reference diagram illustrating local characteristic curves generated by transforming the singular value curve according to one embodiment of the present invention.

FIG. 6 is a reference diagram illustrating local characteristic curves generated by transforming the singular value curve according to one embodiment of the present invention.

Referring to FIG. 6, each local characteristic curve Σ'(i) is generated by reflecting characteristics of each pixel in a common singular value curve Σ. As illustrated in FIG. 6, a common singular value curve 610 (Σ) is transformed into various local characteristic curves 620 and 630 (Σ'(i)). A first characteristic curve 620 is a characteristic curve of a pixel having no blood flow signal, and a second characteristic curve 630 is a characteristic curve of a pixel having a blood flow signal. In the case of the second characteristic curve 630, it can be confirmed that the magnitude (dB) of a singular value order in which the blood flow signal is located has been enhanced and changed. Portion A, which is a portion enhanced due to the blood flow signal, becomes a feature point for the cutoff threshold value.

Figure 7:
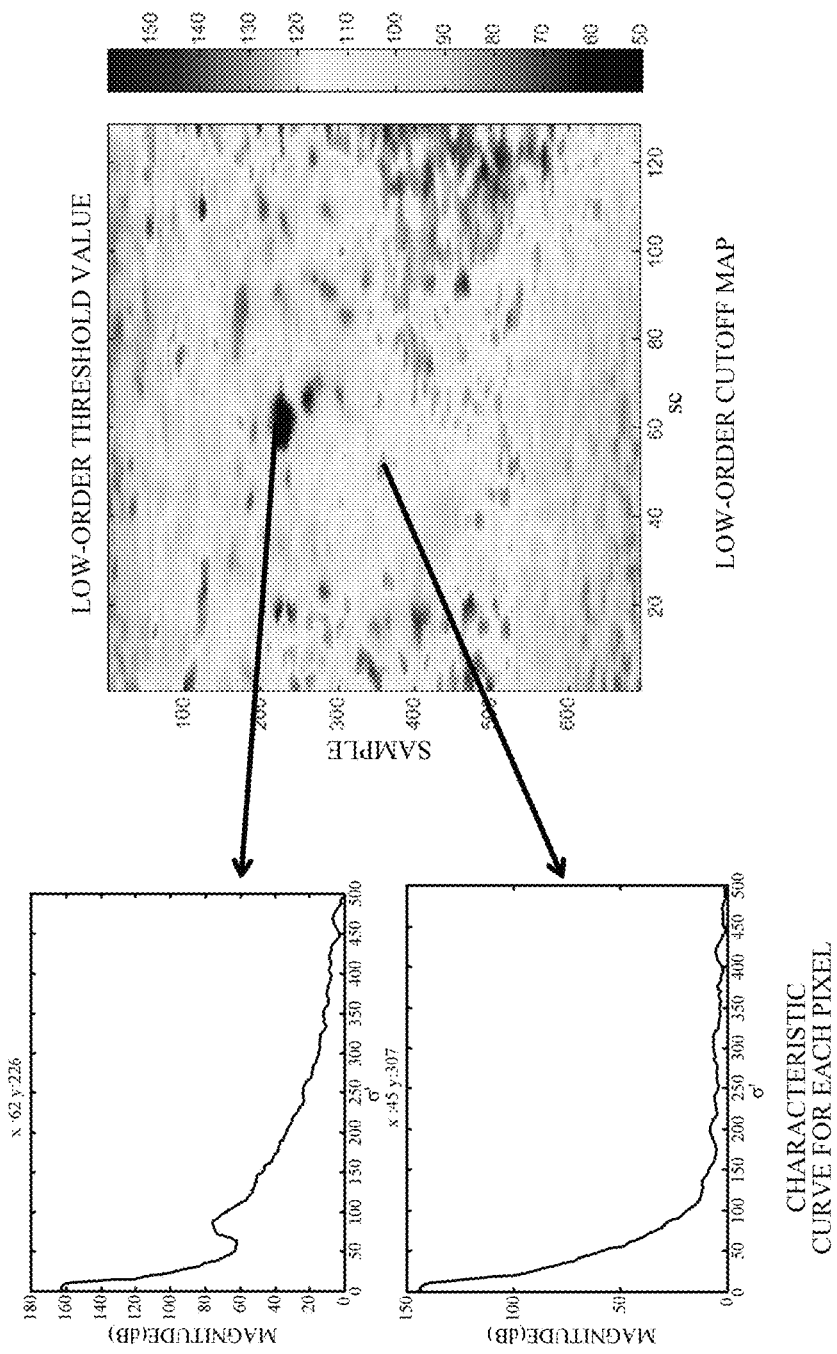
FIG. 7 is a reference diagram illustrating characteristic curves for each pixel and a low-order cutoff map for describing a thresholding method according to one embodiment of the present invention.

FIG. 7 is a reference diagram illustrating characteristic curves for each pixel and a low-order cutoff map for describing a thresholding method according to one embodiment of the present invention.

Referring to FIG. 7, the ultrasound imaging device generates a threshold value map using the threshold values corresponding to the calculated pixel. Here, filtering may be performed on the obtained threshold value map. The filtering may include smoothing, median, weighting, and the like. As illustrated in FIG. 7, a low-order threshold value map represents low-order threshold values for each sample, and the color or brightness of the sample may be distinguished according to the magnitude of the threshold value. The graphs on the left side of FIG. 7 illustrate the characteristic curve of a first pixel (x:62 and y:226) and the characteristic curve of a second pixel (x:45 and y:307) in the low-order threshold value map. In the threshold value map, singular vectors of a pixel having a cutoff threshold value less than a low-order cutoff threshold value or greater than a high-order cutoff threshold value may be masked to zero or weighted by a predetermined value for each pixel FIG. 8 is a flowchart illustrating a clutter filtering method according to one embodiment of the present invention.

Figure 8:
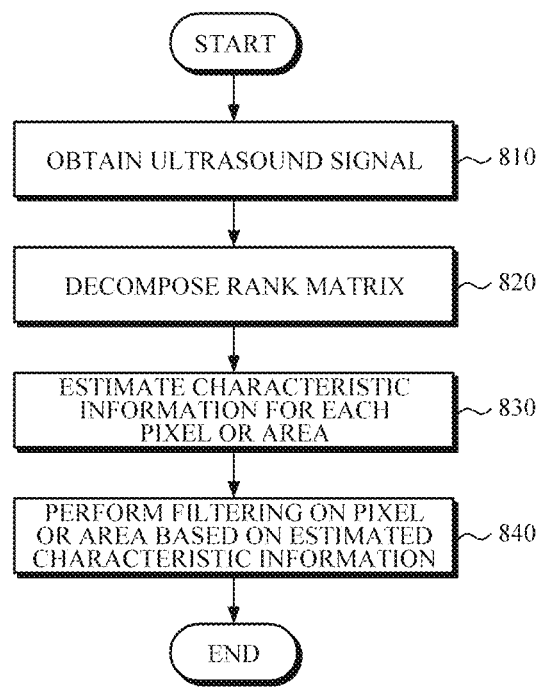
FIG. 8 is a flowchart illustrating a clutter filtering method according to one embodiment of the present invention.

Referring to FIGS. 3 and 8, the ultrasound imaging device obtains ultrasound data from a FOV of an object (810). The obtained ultrasound data may be I/Q data. The ultrasound imaging device generates decomposition data including common scale information by performing rank matrix decomposition once on all of the obtained ultrasound data (820). The rank matrix decomposition according to one embodiment is SVD, and the SVD may be performed on an input data matrix M of all of the ultrasound data to obtain decomposition data decomposed into scale information, spatial information, and time information. In the case of the SVD, the scale information is a singular value matrix Σ composed of singular values representing scale values for each subspace, the spatial information is a spatial vector matrix U composed of spatial vectors corresponding to each of the singular values, and the time information is a transposed matrix $V^T$ of a time vector matrix V composed of time vectors corresponding to each of the singular values.

Subsequently, the ultrasound imaging device estimates local characteristic information by reflecting the spatial information on each pixel to the common scale information (830) and extracts a blood flow signal by performing filtering on each pixel based on the estimated local characteristic information (840). In the operation 830 of estimating the local characteristic information, the ultrasound imaging device according to one embodiment combines spatial vectors U(i) for each pixel constituting the spatial information with common scale information Σ to estimate local characteristic information Σ'(i) in which characteristics for each pixel are reflected. In other words, a scale value curve is generated by configuring singular values in the common scale information, and the generated scale value curve is transformed according to the spatial characteristics of each pixel to generate a local characteristic curve.

In the operation 830 of estimating the local characteristic information, the spatial vector for each pixel constituting the spatial information is filtered in spatial direction, and the filtered spatial vector for each pixel and the common scale information are combined to generate the local characteristic information Σ'(i) in which the common scale information is transformed. In the operation 830 of estimating the local characteristic information, the ultrasound imaging device may adjust the degree of combining between the spatial vector for each pixel and the scale information. For example, the multiplier of the absolute value of the spatial vector for each pixel may be adjusted. The generated characteristic curve may have a scale converted to a log scale or a decibel scale. The generated characteristic curve may be subjected to a smoothing process using a smooth filter, or a moving average process.

Figure 9:
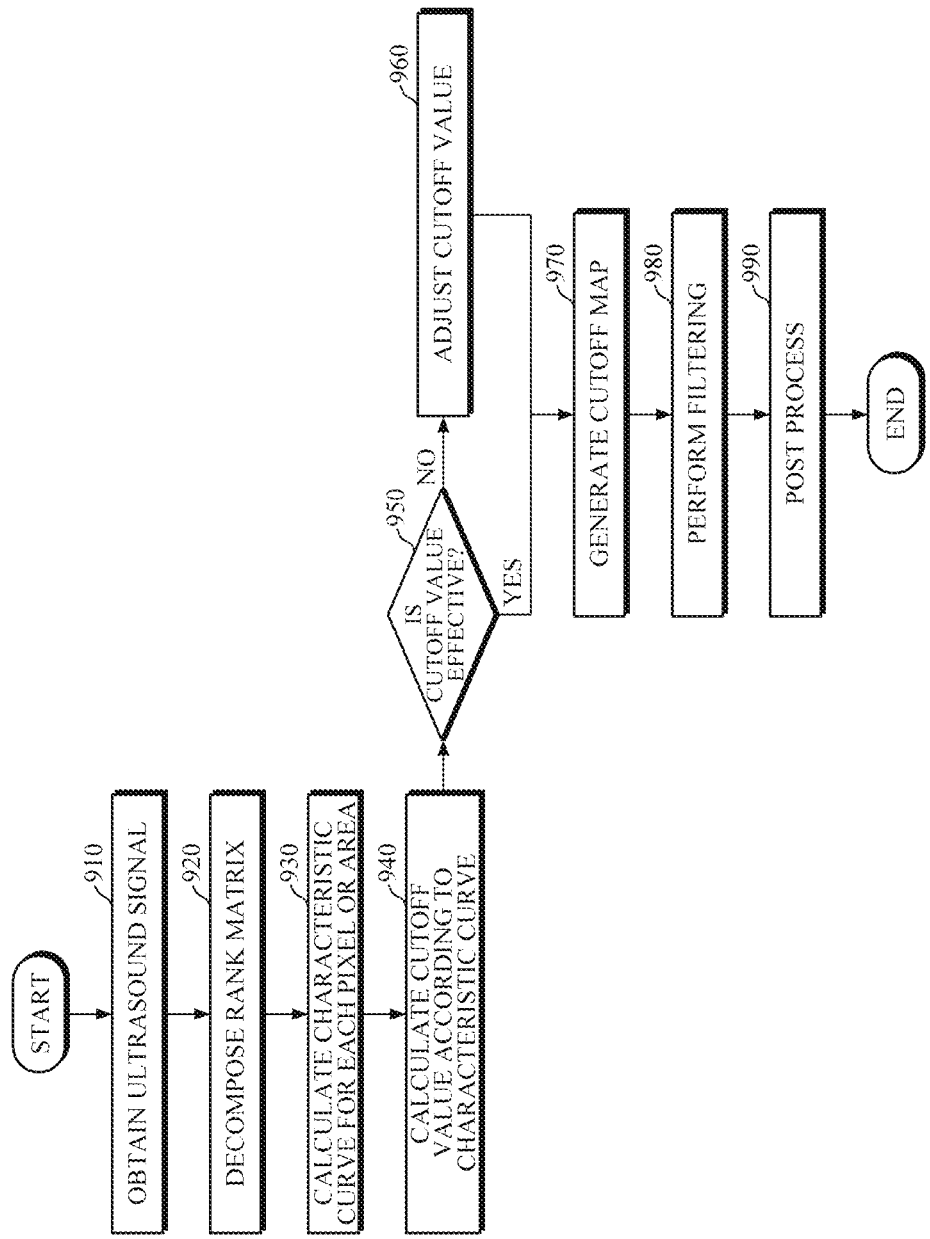
FIG. 9 is a flowchart illustrating a clutter filtering method according to another embodiment of the present invention.

FIG. 9 is a flowchart illustrating a clutter filtering method according to another embodiment of the present invention.

Referring to FIG. 9, an ultrasound imaging device obtains ultrasound data from a FOV of an object (910). Subsequently, decomposition data including common scale information is generated by performing rank matrix decomposition once on all of the obtained ultrasound data (920). The rank matrix decomposition according to one embodiment is SVD, and the SVD may be performed on an input data matrix M of all of the ultrasound data to obtain decomposition data decomposed into scale information, spatial information, and time information.

Subsequently, a local characteristic curve is calculated by reflecting the characteristics of a pixel to the common scale information (930). Next, a cutoff threshold value is calculated according to the characteristic curve (940). Here, cutoff threshold values, which are different for each piece of estimated local characteristic information, are calculated. In the operation 940 of calculating the cutoff threshold value, the ultrasound imaging device calculates the cutoff threshold value using a slope of each scale value order and an average slope in a section of the characteristic curve in each characteristic curve in which the characteristics for each pixel are reflected. For example, for each characteristic curve, the average slope in the section of the characteristic curve is subtracted from the slope in each scale value order, and the scale value order having a minimum value in the curve obtained by accumulating subtracted results is determined as a low-order cutoff threshold value. As another example, the characteristic curve of each pixel is extended using the characteristics of the scale value curve and the low-order cutoff threshold value is determined in the extended characteristic curve.

Subsequently, the cutoff threshold value calculated for each pixel is evaluated to determine whether the cutoff threshold value is effective (950). As an example of an effectiveness determination method, the ultrasound imaging device obtains a Doppler spectrum for the time information generated through the rank matrix decomposition. In addition, a frequency value of each time vector order of the obtained Doppler spectrum is compared with a preset Doppler spectrum frequency value, and the time vector order whose frequency value is greater than the preset Doppler spectrum frequency value or the time vector order having a frequency value whose difference from the preset Doppler spectrum frequency value is less than a preset offset value is set as an effective value. Next, the effectiveness of the cutoff threshold value is evaluated according to whether the cutoff threshold value is greater or less than the effective value.

As another example of the effectiveness determination method, the ultrasound imaging device obtains a Doppler spectrum for the time information generated through the rank matrix decomposition. In addition, a frequency value of each time vector order of the obtained Doppler spectrum is compared with a preset Doppler spectrum frequency value, and a section consisting of time vector orders whose frequency value is greater than the preset Doppler spectrum frequency value or the time vector order having a frequency value whose difference from the preset Doppler spectrum frequency value is less than a preset offset value is set as an effective range. Next, the effectiveness of the cutoff threshold value is evaluated according to whether the cutoff threshold value is included in the set effective range.

When the cutoff threshold value is not effective according to the evaluation result, the cutoff threshold value is adjusted (960). For example, when the cutoff threshold value is not effective according to the evaluation result, the cutoff threshold value calculated using the scale value curve is used as the cutoff threshold value of the corresponding pixel.

Subsequently, the ultrasound imaging device reflects each calculated cutoff threshold value to each pixel to perform local adaptive filtering (980). To this end, the ultrasound imaging device generates a threshold value map composed of the calculated cutoff threshold values for each pixel (970) and performs filtering using the generated threshold value map to separate a blood flow signal from the clutter signal (980).

In the operation 980 of filtering the blood flow signal, the ultrasound imaging device may mask the spatial vectors of a pixel having a cutoff threshold value less than the low-order cutoff threshold value or greater than the high-order cutoff threshold value for each pixel in the threshold value map to zero or weight the spatial vectors with a predetermined value. Next, the ultrasound imaging device may perform post processing (990).

Figure 10:
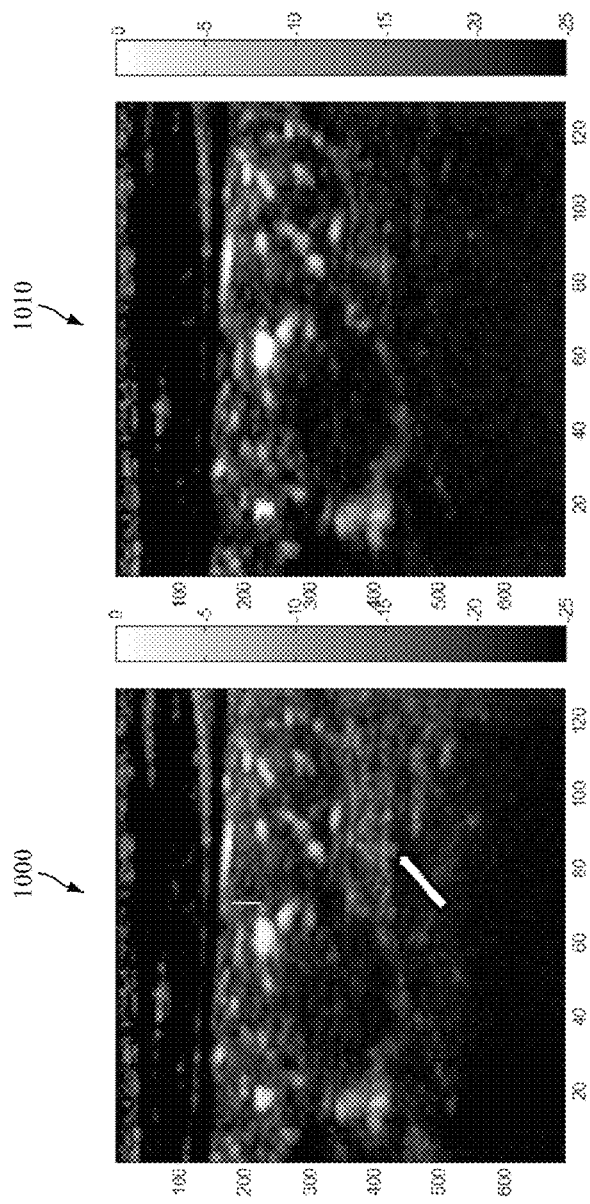
FIG. 10 is a graph showing filtering results when a global singular value decomposition (SVD)-based local adaptive filtering method according to one embodiment of the present invention is used.

FIG. 10 is a graph showing filtering results when the global SVD-based local adaptive filtering method according to one embodiment of the present invention is used.

Referring to an image 1000 in FIG. 10 in which the global SVD method is used, it is confirmed that a tissue signal remains in the image (indicated by an arrow). On the contrary, referring to an image 1010 in which the global SVD-based local adaptive filtering method is used, the tissue signal that remains in the global SVD method is filtered to exhibit improved performance.

Heretofore, the present invention has been described by focusing on the exemplary embodiments. It can be understood by those skilled in the art to which the present invention pertains that the present invention can be implemented in modified forms without departing from the essential feature of the present invention. Therefore, the disclosed embodiments should be considered as illustrative rather than determinative. The scope of the present invention is defined by the appended claims rather than by the foregoing description, and all differences within the scope of equivalents thereof should be construed as being included in the present invention.

The invention claimed is:

1. A clutter filtering method using an ultrasound imaging device, the method comprising:
  obtaining ultrasound data from a field-of-view (FOV) of an object;
  generating decomposition data including common scale information by performing rank matrix decomposition once on all of the obtained ultrasound data;
  estimating local characteristic information by reflecting spatial information on each pixel to the common scale information; and
  extracting a blood flow signal by performing filtering on each pixel based on the estimated local characteristic information,
  wherein the common scale information is a unique value common to all pixels.

2. The method of claim 1, wherein
  the rank matrix decomposition is singular value decomposition (SVD), and the SVD is performed on an input data matrix of all of the ultrasound data to obtain decomposition data decomposed into scale information, spatial information, and time information, and
  the scale information is a singular value matrix composed of singular values representing scale values for each subspace, the spatial information is a spatial vector matrix composed of spatial vectors corresponding to each of the singular values, and the time information is a transposed matrix of a time vector matrix composed of time vectors corresponding to each of the singular values.

3. The method of claim 1, wherein the estimating of the local characteristic information includes combining spatial vectors for each pixel constituting the spatial information with the common scale information to estimate the local characteristic information in which characteristics for each pixel are reflected.

4. The method of claim 3, wherein the estimating of the local characteristic information includes:
  performing filtering on the spatial vectors for each pixel constituting the spatial information in a spatial direction; and
  combining the filtered spatial vector for each pixel with the common scale information to generate local characteristic information of which the common scale information is transformed.

5. The method of claim 4, wherein the estimating of the local characteristic information further includes adjusting the degree of combining between the spatial vector for each pixel and the scale information.

6. The method of claim 4, wherein the estimating of the local characteristic information further includes:
  generating a characteristic curve by configuring characteristic values for each pixel; and
  converting the generated characteristic curve to have a log scale or a decibel scale.

7. The method of claim 6, wherein the estimating of the local characteristic information further includes at least one of:
  performing a smoothing process on the generated characteristic curve using a smooth filter; and
  performing a moving average process on the generated characteristic curve.

8. The method of claim 1, wherein the estimating of the local characteristic information includes:
  generating a scale value curve by configuring scale values in the common scale information; and
  generating a local characteristic curve by transforming the generated scale value curve according to a spatial characteristic of each pixel.

9. The method of claim 1, wherein the extracting of the blood flow signal includes:
  calculating cutoff threshold values that are different for each piece of the estimated local characteristic information; and
  performing local adaptive filtering by reflecting each of the calculated cutoff threshold values to each pixel.

10. The method of claim 9, wherein the calculating of the cutoff threshold value includes calculating the cutoff threshold value using a slope of each scale value order and an average slope in a section of a characteristic curve in each characteristic curve in which characteristics of each pixel are reflected.

11. The method of claim 10, wherein the calculating of the cutoff threshold value includes, for each characteristic curve, subtracting the average slope in the section of the characteristic curve from the slope in each scale value order and determining the scale value order having a minimum value in a curve obtained by accumulating subtracted results as a low-order cutoff threshold value.

12. The method of claim 9, wherein the calculating of the cutoff threshold value includes extending a characteristic curve of each pixel using characteristics of a scale value curve and determining a low-order cutoff threshold value in the extended characteristic curve.

13. The method of claim 9, wherein the extracting of the blood flow signal further includes:
  evaluating the cutoff threshold values calculated for each pixel; and
  adjusting the cutoff threshold values when the cutoff threshold values are not effective according to the evaluation result.

14. The method of claim 13, wherein the evaluating of the cutoff threshold value includes:
  obtaining a Doppler spectrum for time information generated through the rank matrix decomposition;
  comparing a frequency value of each time vector order of the obtained Doppler spectrum with a preset Doppler spectrum frequency value to set the time vector order whose frequency value is greater than the preset Doppler spectrum frequency value or the time vector order having a frequency value whose difference from the preset Doppler spectrum frequency value is less than a preset offset value as an effective value; and evaluating effectiveness of the cutoff threshold value according to whether the cutoff threshold value is greater or less than the effective value.

15. The method of claim 13, wherein the evaluating of the cutoff threshold value includes:
   obtaining a Doppler spectrum for time information generated through the rank matrix decomposition;
   comparing a frequency value of each time vector order of the obtained Doppler spectrum with a preset Doppler spectrum frequency value to set a section consisting of time vector orders whose frequency value is greater than the preset Doppler spectrum frequency value or the time vector order having a frequency value whose difference from the preset Doppler spectrum frequency value is less than a preset offset value as an effective range; and
   evaluating effectiveness of the cutoff threshold value according to whether the cutoff threshold value is included in the set effective range.

16. The method of claim 13, wherein the adjusting of the cutoff threshold value includes using the cutoff threshold value calculated using a scale value curve as the cutoff threshold value of the corresponding pixel when the cutoff threshold value is not effective according to the evaluation result.

17. The method of claim 9, wherein the performing of the local adaptive filtering includes:
   generating a threshold value map composed of the calculated cutoff threshold values for each pixel; and
   separating the blood flow signal from a clutter signal by performing filtering using the generated threshold value map.

18. The method of claim 17, wherein the performing of the local adaptive filtering further includes performing filtering on the generated cutoff map.

19. The method of claim 17, wherein the separating of the blood flow signal includes, in the threshold value map, masking spatial vectors of a pixel having a cutoff threshold value less than a low-order cutoff threshold value or greater than a high-order cutoff threshold value to zero or weighting the spatial vectors by a predetermined value for each pixel.

20. An ultrasound imaging device comprising:
   a signal obtaining unit configured to transmit an ultrasound signal to an object and receive the ultrasound signal reflected from the object; and
   a processor configured to estimate local characteristic information by reflecting spatial information on each pixel to common scale information generated by performing rank matrix decomposition once on obtained ultrasound data and extract a blood flow signal by performing filtering on each pixel based on the estimated local characteristic information,
   wherein the common scale information is a unique value common to all pixels.

21. The ultrasound imaging device of claim 20, wherein the processor includes:
   a data decomposition unit configured to generate decomposition data including spatial information, time information, and common scale information by performing the rank matrix decomposition on all of the obtained ultrasound data;
   a data conversion unit configured to estimate the local characteristic information in which characteristics of each pixel are reflected by combining spatial vectors of the pixel constituting the spatial information with the common scale information;
   a cutoff calculation unit configured to calculate cutoff threshold values that are different for each piece of the estimated local characteristic information; and
   a filtering unit configured to perform local adaptive filtering by reflecting each of the calculated cutoff threshold values to each pixel.

22. The ultrasound imaging device of claim 21, wherein the data conversion unit includes:
   a combining unit configured to combine a spatial vector for each pixel constituting the spatial information with the common scale information to generate the local characteristic information of which the common scale information is transformed; and
   a combining adjusting unit configured to adjust a degree of combining the spatial vector for each pixel and the scale information for combining.

23. The ultrasound imaging device of claim 21, wherein the cutoff calculation unit calculates the cutoff threshold values using a slope of each scale value order and an average slope in a section of a characteristic curve in each characteristic curve in which characteristics of each pixel are reflected.

24. The ultrasound imaging device of claim 21, wherein the filtering unit generates a threshold value map composed of the calculated cutoff threshold values for each pixel and masks the spatial vectors of the pixel having a cutoff threshold value less than a low-order cutoff threshold value or greater than a high-order cutoff threshold value for each pixel in the threshold value map to zero or weights the spatial vectors with a predetermined value.

* * * * *